United States Patent [19]

Drent

[11] Patent Number: 4,960,906

[45] Date of Patent: Oct. 2, 1990

[54] PROCESS FOR THE PREPARATION OF LACTONES FROM HIGHER ALKENOLS

[75] Inventor: Eit Drent, Amsterdam, Netherlands

[73] Assignee: Shell Oil Company, Houston, Tex.

[21] Appl. No.: 342,831

[22] Filed: Apr. 25, 1989

[30] Foreign Application Priority Data

May 10, 1988 [GB] United Kingdom ................. 8811024

[51] Int. Cl.$^5$ ................... C07D 309/30; C07D 307/32
[52] U.S. Cl. ..................................... 549/273; 549/295
[58] Field of Search ................................ 549/273, 295

[56] References Cited

U.S. PATENT DOCUMENTS 4,602,114  7/1986  Matson et al. ....................... 349/266
4,634,780  1/1987  Alper et al. .......................... 549/273

FOREIGN PATENT DOCUMENTS 0106379  8/1983  European Pat. Off.
0176370  4/1986  European Pat. Off. ............ 549/273

OTHER PUBLICATIONS

"Scope of Pd-Catalyzed Cyclo-carbonylation of Unsaturated Alcohols to α-substituted Lactones", ACS, Mar. 1980, pp. 23-28.

Jouranl Chem. Soc., Chem. Comm., No. 8, Apr. 15, 1985, 511-512, London, GB.

Norton, J., "Scope of the Pd-Catalyzed Cyclocarbonylation of Unsaturated Alcohol to α-Substituted Lactones", ACS, Mar. 23-28, 1980, pp. 368-371, (Houston Meeting).

Ansell et al., "The Cyclisation of Olefinic Acids to Ketones and Lactones", Quarterly Review, 1964, pp. 211-224.

Primary Examiner—Richard L. Raymond
Assistant Examiner—Ba K. Trinh

[57] ABSTRACT

Process for the preparation of lactones, having 4 or 5 carbon atoms in the ring by reacting a higher alkenol with a carbon monoxide containing gas in the presence of a catalytic system comprising
  (a) a palladium compound,
  (b) a bidentate phosphine, arsine and/or stibine, and
  (c) a protonic acid having a $pK_a < 2$.

11 Claims, No Drawings

PROCESS FOR THE PREPARATION OF LACTONES FROM HIGHER ALKENOLS

Field of the Invention

The present invention relates to the production of lactones having 4 or 5 carbon atoms in the ring by the reaction of higher alkenols, in which the hydroxy group is 5 or more carbon atoms remote from the double bond, with carbon monoxide.

BACKGROUND OF THE INVENTION

From U.S. Pat. No. 4,634,780, it is known that lactones having a 5 or 6 membered ring can be prepared by reacting, inter alia, an alkenol containing 5 or more aliphatic carbon atoms with carbon monoxide. However, the following restriction is made with respect to the alkenols which may be used in the process: the olefinic unsaturation should not be located more than three carbon atoms from the hydroxy substituent. Said patent specification does not teach in any way the conversion of alkenols having 5 or more aliphatic carbon atoms in which the aliphatic unsaturation is more than 3 carbon atoms removed from the hydroxy substituent. Moreover the process described in said patent specification should be carried out in the presence of oxygen in order to obtain acceptable, yet moderate, product yields. The catalytic system used in this reaction consists of: a protonic acid, one or more metals selected from the group consisting of palladium, rhodium, ruthenium, iridium cobalt or compounds thereof, and one or more metals selected from the group consisting of copper, molybdenum and iron.

It will be appreciated that the before-mentioned process has several unfavorable characteristics i.e. as starting compounds only alkenols can be used which have the olefinic unsaturation no more than three carbon atoms removed from the hydroxy substituent and a complex catalyst system is used.

Consequently, due to an increasing demand for lactone products which can be used as solvents and useful intermediates for chemical synthesis, there is a big need for a more universal and economical production process.

It has now been found that substituted or unsubstituted lactones having four or five carbon atoms in the ring can be produced with improved selectivity and improved yields by reaction of substituted or unsubstituted alkenols, in which the hydroxy group is 5 or more carbon atoms remote from the double bond, in the presence of a relatively simple catalytic system which is believed to cause isomerization in situ by shifting the carbon to carbon double bond of an alkenol, in which the olefinic unsaturation is more than three carbon atoms removed from the hydroxy substituent, to an alkenol in which the olefinic unsaturation is three carbon atoms removed from the hydroxy substituent.

SUMMARY OF THE INVENTION

This invention relates to a process for the preparation of lactones having four or five carbon atoms in the ring or a mixture thereof, which process comprises reacting an alkenol, having the general formula:

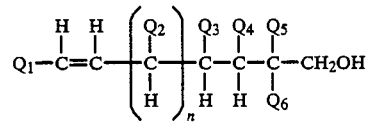

in which n is 0 or an integer from 1 to 25 and in which $Q_1$ represents a hydrogen or an alkyl group having in the range of from 1 to 30 carbon atoms and in which $Q_2$, $Q_3$, $Q_4$, $Q_5$ and $Q_6$ each independently represent a hydrogen atom or a lower alkyl group having 1 to 4 carbon atoms with the proviso that $Q_3$ and $Q_4$ do not represent a lower alkyl group simultaneously, with a carbon monoxide-containing gas and a catalytic system comprising:

(a) a palladium compound,
(b) a bidentate phosphine, arsine or stibine, and
(c) a protonic acid having a $pK_a$ less than 2, wherein said catalytic system has a molar ratio of component (a) to said alkenol, in which the hydroxy group is five or more carbon atoms remote from the double bond, of from about 1:10 to about 1:1.000.000, a molar ratio of total phosphorus to component (c) of lower than about 2, a molar ratio of total phosphorus to component (a) ranging from about 2 to about 400, and a molar ratio of bidentate compound to component (a) of at least about 1.

DESCRIPTION OF THE PREFERRED EMBODIMENTS

It will be appreciated that the process of the present invention is very attractive because it is carried out in the presence of a relatively simple catalyst system. Moreover, this process shows an extremely high selectivity to lactones having four or five carbon atoms in the ring thus minimizing the formation of byproducts.

More particularly it is attractive that the process of the present invention should be carried out without the presence of oxygen thus minimizing the danger of explosion and the aselective oxidation of carbon monoxide to carbon dioxide.

The lactones produced according to the present invention are interesting solvents and very useful intermediates. For example, lactones can be converted to enol ethers, hydroxylesters and lactams.

As will be appreciated, the process according to the present invention may be carried out using a variety of alkenols in which the hydroxy group is 5 or more carbon atoms remote from the double bond. It is understood that the alkanols can be substituted with one or more substituents which do not interfere with the reaction. The process can be schematically represented by means of equation A:

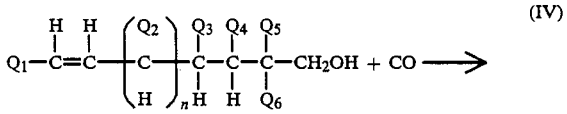

(IV)

-continued

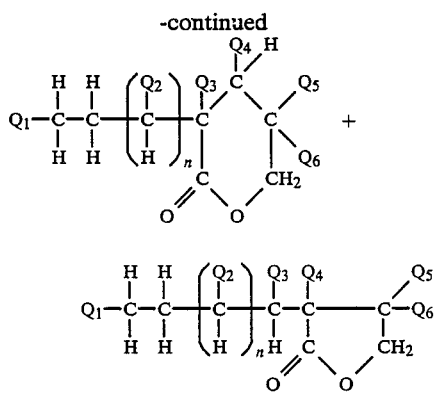

in which n is 0 or an integer from 1 to 25 and in which $Q_1$ represents hydrogen or an alkyl group having in the range of from 1 to 30 carbon atoms and in which $Q_2$, $Q_3$, $Q_4$, $Q_5$, and $Q_6$ each independently represent a hydrogen atom or a lower alkyl group, with the proviso that $Q_3$ and $Q_4$ do not represent an alkyl group simultaneously.

With the term lower alkyl as used throughout the specification is meant an alkyl containing 1-4 carbon atoms. Among these alkyl groups methyl groups and ethyl groups are preferred in particular methyl groups. However, $Q_2$, $Q_3$, $Q_4$, $Q_5$, and $Q_6$ most preferably represent hydrogen atoms.

More particularly, it will be appreciated that the carbon monoxide molecule involved in the reaction according to equation A will only bind to a secondary carbon atom involved in the carbon to carbon double bond. Therefore, the product of the general formula V can only be formed if $Q_3$ represents hydrogen and the product of the general formula VI can only be formed if $Q_4$ represents hydrogen. Consequently, a mixture of the products V and VI is formed if $Q_3$ and $Q_4$ both represent hydrogen.

Alkenols which are useful reactants are for example: 4-penten-1-ol, 5-hexen-1-ol, 4-hexen-1-ol, 6-hepten-1-ol, 5-hepten-1-ol, 4-hepten-1-ol 7-octen-1-ol, 6-octen-1-ol, 5-octen-1-ol, 4-octen-1-ol, 8-nonen-1-ol, 7-nonen-1-ol, 6-nonen-1-ol, 5-nonen-1-ol, 4-nonen-1-ol, 9-decen-1-ol, 8-decen-1-ol, 7-decen-1-ol, 6-decen-1-ol, 5-decen-1-ol, 4-decen-1-ol, 10-undecen-1-ol, 9-undecen-1-ol, 8-undecen-1-ol, 9-undecen-1-ol, 11-dodecen-1-ol, 10 dodencen-1-ol, 9 dodecen-1-ol, 8-dodencen-1-ol, 7-dodecen-1-ol, 6-dodecen-1-ol, 5-dodencen-1-ol, 4-dodencen-1-ol, 13-tetradecen-1-ol, 12-tetradecen-1-ol, 11-tetradecen-1-ol, 10-tetradecen-1-ol, 9-tetradecen-1-ol, 8-tetradecen-1-ol, 7-tetradecen-1-ol, 6-tetradecen-1-ol, 5-tetradecen-1-ol, 4-tetradecen-1-ol, 14-pentadecen-1-ol, 15-hexadecen-1-ol, 16-heptadecen-1-ol, 17-octadecen-1-ol, 9-octadecen-1-ol, 18-nonadecen-1-ol, 19-eicosen-1-ol, and 20-heneicosen-1-ol.

The process according to the present invention is carried out in the liquid phase in which the palladium compound may be heterogeneous but is preferably homogeneous. Suitable homogeneous palladium compounds are the palladium(II) salts of for instance, nitric acid, sulfuric acid, or preferably of alkanoic acids having no more than 12 carbon atoms per molecule. A preferably used palladium compound is palladium(II) acetate.

Other examples of suitable palladium(II) compounds are palladium(II) formate and palladium(II) propanoate.

Salts of hydrohalogenic acids may also be used in principle but are not preferred due to their corrosive properties.

Moreover, palladium complexes may be used, for instance palladium acetylacetonate, tetrakistriphenylphosphine palladium acetate or bis-triphenylphosphine-palladium sulfate. A mixture of palladium compounds may be used as component (a).

It has been found that the process according to the present invention allows the preparation of lactones having 4 or 5 carbon atoms in the ring with an extremely high selectivity. It is understood that the lactones prepared can be unsubstituted or substituted with one or more substituents which do not interfere with the reaction.

The selectivity to a desired compound can be expressed as 100 x p:q, in which "p" is the amount of starting compound that has been converted into that desired compound and "q" is the total amount of starting compound that has been converted.

As before-mentioned component (b) a bidentate chelating ligand or a combination of a bidentate chelating ligand and a monodentate chelating ligand may be used.

The bidentate chelating ligand comprises an organic compound containing as coordinating atoms at least two atoms of phosphorus, arsenic, or antimony which are connected through a divalent organic bridging group having at least two carbon atoms in the bridge.

The two or more coordinating atoms may be the same or different, for example two phosphorus atoms, an arsenic and a phosphorus atom or an arsenic and an antimony atom.

The bidentate chelating ligand preferably has the general formula I:

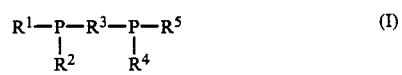

in which $R^1$, $R^2$, $R^4$ and $R^5$ represent identical or different hydrocarbon groups and the bridging group $R^3$ represents a chain consisting of two to six carbon atoms. It is understood that the hydrocarbon groups and the budging group can be substituted with one or more substituents which do not interfere with the reaction.

Any substituents present in the bidentate chelating ligand preferably do not cause steric hindrance to the formation of complex compounds with the palladium-(II) compound.

Hydrocarbon groups $R^1$, $R^4$ and $R^5$ will as a rule contain 2 to 18 carbon atoms, preferably 6 to 14 carbon atoms. Aryl groups are the most suitable, in particular the phenyl group. Preferred bridging groups —$R^3$— are those having the formula $-(R^6R^7)-_n$ in which ($R^6$ and $R^7$) are hydrogen atoms or hydrocarbon groups preferably offering no steric hindrance and n is an integer of at least two, preferably not more than 5, and most preferably 2, 3 or 4. Substituents $R^6$ and $R^7$ are preferably hydrogen atoms. The bridging groups $R^3$ may also form part of a cyclic structure, e.g. an aromatic or cycloaliphatic group, the carbon to carbon bond or bonds in the bridge may be saturated or unsaturated and in the bridge or in the cyclic or non-cyclic groups attached to the bridge one or more hetero atoms, e.g. sulfur, oxygen, iron or nitrogen atoms, may replace carbon atoms, provided that both phosphorus atoms are linked to a carbon atom remain present in the bridge. Examples of suitable chelating ligands are:
1,3-di(diphenylphosphino)propane, 1,4-di(diphenylphosphino)butane,
2,3-dimethyl-1,4-di(diphenylphosphino)butane,
1,5-di(methylphenylphosphino)pentane,
1,4-di(dicyclohexylphosphino)butane,
1,5-di(dinaphthylphosphino)pentane,
1,3-di(di-p-tolylphosphino)propane,
1,4-di(di-p-methoxyphenylphosphino)butane,
1,2-di(diphenylphosphino)ethene,
2,3-di(diphenylphosphino)-2-butene,
1,3-di(diphenylphosphino)-2-oxopropane,
2-methyl-2-(methyldiphenylphosphino)-1,3-di(diphenylphosphino)propane,
o,o'-di(diphenylphosphino)biphenyl,
1,2-di(diphenylphosphino)benzene,
2,3-di(diphenylphosphino)naphthalene,
1,2-di(diphenylphosphino)cyclohexane,
2,2-dimethyl-4,5-di(diphenylphosphino)dioxolane and

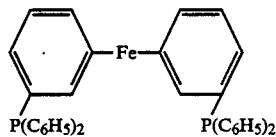

Very good results have been obtained with 1,4-di(diphenylphosphino)butane or 1,4-di(diphenylphosphino)propane. A mixture of chelating ligands of the general formula I may be used.

The monodentate phosphine has the general formula II:

in which $R^8$, $R^9$, and $R^{10}$ each individually represent an aryl group. It is understood that the aryl group can be substituted with one or more substituents which do not interfere with the reaction.

The substituted or unsubstituted aryl groups $R^8$, $R^9$ and $R^{10}$ of the phosphine of the general formula II each preferably contain not more than 18, in particular in the range of from 6 to 14 carbon atoms. Examples of suitable $R^8$, $R^9$ and $R^{10}$ groups are the naphthyl group and in particular, the phenyl group. Suitable substituents are halogen atoms and alkyl, aryl, alkoxy, carboxy, carbalkoxy, acyl, trihalogenmethyl, cyano, dialkylamino, sulfonylalkyl and alkanoyloxy groups.

Examples of suitable phosphines are tri-p-tolylphosphine, tri(p-chlorophenyl)phosphine, tri-p-methoxyphenylphosphine, o-diphenylphosphinobenzoic acid and preferably triphenylphosphine. A mixture of phosphines of the general formula II may be used.

The protonic acid having a $pK_a$ of less than 2 preferably has an anion which is non-coordinating, by which is meant that little or no covalent interaction takes place between the palladium and the anion of the protonic acid.

A preferred group of acids has the general formula III

in which X represents a sulfur or a chlorine atom and, if X represents a chlorine atom, $R^{11}$ represents an oxygen atom and, if X represents a sulfur atom, $R^{11}$ represents an OH group or an optionally substituted hydrocarbon group.

When the hereinbefore stated acids are used in the process according to the invention, the anions of the acids can be considered to be non-coordinating.

In the acids having the general formula III, the hydrocarbon group represented by $R^{11}$ is preferably an alkyl, aryl, aralkyl or alkaryl group having 1–30, in particular 1–14, carbon atoms. It is understood that the hydrocarbon group can be substituted with one or more substituents which do not interfere with the reaction. The hydrocarbon group may, for example, be substituted with halogen atoms, in particular fluorine atoms. Preferred acids of the general formula III are perchloric acid, sulfuric acid, p-toluenesulfonic acid and trifluoromethanesulfonic acid. p-Toluenesulfonic acid is particularly preferred. Another suitable acid is 2-hydroxypropane-2-sulfonic acid. The acid of the general formula III can also be an ion exchanger containing sulfonic acid groups, such as, for example, Amberlite 252 H ("Amberlite" is a trade name). In that case, the hydrocarbon group $R^{11}$ is a polymeric hydrocarbon group, for example, a polystyrene group substituted with sulfonic acid groups. Further examples of suitable acids are those that can be formed, possibly in situ, by interacting a Lewis acid such as, $BF_3$, $AsF_5$, $SbF_5$, $PF_5$, $TaF_5$ or $NbF_5$ with a Broensted acid such as, a hydrohalogenic acid, in particular HF, fluorosulfonic acid, phosphoric acid or sulfuric acid. Specific examples of acids of the latter type are $H_2SiF_6$, $HBF_4$, $HPF_6$ and $HSbF_6$. Examples of suitable sulfonic acids are fluorosulfonic acid and chloro-sulfonic acid. Other examples of suitable acids are trichloroacetic acid, trifluoroacetic acid, dichloroacetic acid and difluoroacetic acid. A mixture of protonic acids having a $pK_a$ of less than 2 may be used as component (c).

The process according to the invention is suitably carried out in the presence of a solvent, which is preferably aprotic. Examples of such solvents are hydrocarbons, such as hexane, heptane, octane, benzene, toluene, the three xylenes, ethylbenzene, cumene, cyclohexane and decalin; halogenated hydrocarbons, such as dichloromethane, chloroform, 1,2-dichloroethane, perfluoroalkanes, chlorobenzene and the three dichlorobenzenes; sulfones such as diethyl sulfone, diisopropyl sulfone and tetrahydrothiophene 1,1-dioxide (also referred to as "sulfolane"), N,N-dialkyl-substituted amides such as N,N-dimethylformamdide and N-methylpyrrolidone., esters such as methyl benzoate, ethyl acetate and amyl acetate; ethers such as diethyl ether, 3,6-dioxaoctane, methyl tert-butylether, tetrahydrofuran, diisopropyl ether, 1,4-dioxane, 2,5,8-trioxanonane (also referred to as "diglyme"), diphenyl ether and anisole. Very good results have been obtained with ethers.

In the process according to the invention as carbon monoxide containing gas may be used carbon monoxide in pure form or diluted with an inert gas, such as nitrogen, noble gases or carbon dioxide or hydrogen, e.g. in the form of synthesis gas.

Generally, the presence of more than 20% hydrogen is undesirable, since under the reaction conditions it may cause hydrogenation of the olefinic compound. Generally, the preference is given to carbon monoxide or a carbon monoxide containing gas which contains less than 5% hydrogen.

The process according to the present invention can be carried out at a temperature and a pressure which are not critical and may vary within wide ranges. The temperature may suitably vary in the range of from 20° C. to 250° C. and preferably from 50° C. to 200° C. The pressure may suitably vary in the range of from 1 to 100 bar and preferably from 10 to 75 bar.

Reaction time may vary over a wide range from about 15 minutes to 8 hours.

The process according to the present invention may be carried out batchwise, semi-continuously or continuously. When operating batchwise, the catalytic system, the starting alkenol and the solvent are charged to a reactor to form a liquid phase therein, the reactor is pressurized with carbon monoxide and heated to the desired temperature. When operating continuously, the liquid components can be charged to the reactor continuously to form a liquid phase therein and the carbon monoxide continuously introduced into the reactor to contact the liquid phase containing the catalyst. The gaseous reactants can be withdrawn from the reactor as a separate effluent, cooled, depressurized and the carbon monoxide can be recycled for further contacting.

The lactones may be isolated from the reaction mixture in any suitable manner, for example by means of extraction or by distillation, obtaining a distillate fraction containing the lactones and a bottom fraction containing the catalytic system. Suitably, a solvent is chosen that substantially remains in the bottom fraction. Preferably, at least a portion of the bottom fraction containing solvent and catalytic system is re-used in the process according to the invention.

The following Examples further illustrate the invention, however, without restricting the scope thereof to these specific embodiments.

EXAMPLE 1

A 300 ml magnetically stirred Hastelloy autoclave ( "Hastelloy" is a trade mark ) was charged with the following materials:
anisole 40 ml
10-undecen-1-ol 10 ml
$Pd(Ac)_2 0,4$ mmol
$P(Ph)_2—(CH_2)_4—P(Ph)_2 1,6$ mmol
para toluene sulfonic acid 4 mmol The autoclave was flushed with carbon monoxide, pressurized with carbon monoxide until a partial pressure of 40 bar was obtained, heated to a temperature of 140° C. and kept at this temperature for 5 hours.

The autoclave was cooled to an ambient temperature and vented and the content was analyzed by gas liquid chromatography. At the end of the reaction, the conversion of 10-undecen-1-ol was 65 % with a selectivity to 3-octyl-2-tetrahydro furanon of 68% and to 3-heptyl-2-tetrahydro pyranon of 19%.

EXAMPLE 2

The experiment was carried out as described in Example 1 with the difference that 2 mmol $PPh_3$ was additionally added to the reaction mixture.

At the end of the reaction, the conversion of 10-undecen-1-ol was 44% with a selectivity to 3-octyl-2-tetrahydro furanon of 69% and to 3-heptyl-2-tetrahydro pyranon of 23%.

EXAMPLE 3

The experiment was carried out as described in Example 1 with 9-octadecen-1-ol (oleyl alcohol) an alkenol.

At the end of the reaction, the conversion of 9-octadecen-1-ol was 86% with a selectivity of to 3-pentadecyl-2-tetra hydrofuranon of 66% and to 3-tetradecyl-2-tetrahydropyranon of 25%.

I claim:

1. A process for the preparation of lactones having four or five carbon atoms in the ring or a mixture thereof, which process comprises reacting an alkenol, having the general formula:

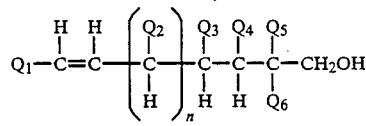

wherein n is 0 or an integer from 1 to 25 and wherein $Q_1$ represents a hydrogen atom or an alkyl group having in the range of from 1 to 30 carbon atoms and wherein $Q_2$, $Q_3$, $Q_4$, $Q_5$ and $Q_6$ each independently represent a hydrogen atom or a lower alkyl group having 1 to 4 carbon atoms with the proviso that $Q_3$ and $Q_4$ do not represent a lower alkyl
group simultaneously, with a carbon monoxide-containing gas and a catalytic system which comprises:
(a) palladium compound
(b) a bidentate compound selected from the group consisting of phosphine, arsine and stibine, and
(c) a protonic acid having a $pK_a$ less than 2, wherein said catalytic system has a molar ratio of component (a) to said alkenol, in which the hydroxy group is five or more carbon atoms remote from the double bond, of from about 1:10 to about 1:1.000.000, a molar ratio of total phosphorus to component (c) which is lower than about 2, a molar ratio of total phosphorus to component (a) which is in the range of from about 2 to about 400 and a molar ratio of said bidentate compound to component (a) of at least about 1.

2. The process of claim 1 wherein said palladium compound is a palladium(II) salt of an alkanoic acid having no more than 12 carbon atoms per molecule.

3. The process of claim 1 wherein component (b) is a chelating ligand comprising an organic compound containing as coordinating atoms at least two atoms selected from the group consisting of phosphorus, arsenic or antimony which are connected through a divalent organic bridging group having at least two carbon atoms in the bridge.

4. The process of claim 3 wherein the chelating ligand has the general formula I

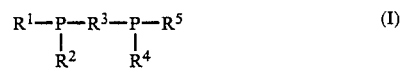

in which $R^1$, $R^2$, $R^4$ and $R^5$ represent identical or different hydrocarbon groups and $R^3$ represents a chain consisting of two to six carbon atoms.

5. The process of claim 4 wherein the chelating ligand is selected from the group consisting of 1,4-di(diphenylphosphino)butane and 1,3-di(diphenylphosphino)propane.

6. The process of claim 1 wherein said catalyst system additionally comprises a monodentate chelating ligand having the
general formula II

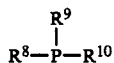

wherein $R^8$, $R^9$, and $R^{10}$ each individually represent an aryl group.

7. The process of claim 6 wherein the aryl groups of the monodentate chelating ligand compound are phenyl groups.

8. The process of claim 1 wherein component (c) is a protonic acid having a $pK_a$ of less than 2 and having a non-coordinating anion.

9. The process of claim 8 wherein component (c) has the general formula III

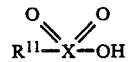

in which X represents a sulfur or a chlorine atom and, if X represents a chlorine atom, $R^{11}$ represents an oxygen atom and, if X represents a sulfur atom, $R^{11}$ represents an OH group or hydrocarbon group.

10. The process of claim 9 wherein component (c) is p-toluene sulfonic acid.

11. The process of claim 1 wherein said process is carried out at a temperature of from about 20° C. to about 250° C. and at a pressure in the range from 1 to about 100 bar.

* * * * *